United States Patent
Prater

(10) Patent No.: US 7,172,065 B2
(45) Date of Patent: Feb. 6, 2007

(54) SHRINK WRAP WITH SAMPLE HOLES

(75) Inventor: Rodney L. Prater, Oak Creek, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 436 days.

(21) Appl. No.: 10/243,176

(22) Filed: Sep. 13, 2002

(65) Prior Publication Data

US 2004/0050741 A1 Mar. 18, 2004

(51) Int. Cl.
*B65D 75/00* (2006.01)

(52) U.S. Cl. .......................................... 206/0.5; 206/497

(58) Field of Classification Search ................ 206/497, 206/443, 459.1, 0.5, 576
See application file for complete search history.

(56) References Cited

U.S. PATENT DOCUMENTS

| 3,388,788 A | 6/1968 | Hellem |
| 3,804,235 A | 4/1974 | Anderson |
| 4,812,317 A | 3/1989 | Taylor |
| 4,815,603 A | 3/1989 | Harris |
| 4,873,814 A | 10/1989 | Harris |
| 4,941,572 A | 7/1990 | Harris |
| 5,171,593 A | 12/1992 | Doyle |
| 5,372,494 A | 12/1994 | Vaughan |
| 5,569,511 A | 10/1996 | Spector |
| 5,857,952 A * | 1/1999 | Gilbert ........................ 493/218 |
| 5,879,151 A | 3/1999 | Schultz et al. |
| 5,914,144 A | 6/1999 | Wolfe et al. |
| 5,985,387 A * | 11/1999 | Mori et al. ................. 428/34.9 |
| 5,992,630 A | 11/1999 | Brown et al. |
| 6,020,823 A | 2/2000 | DeCicco |
| D424,430 S | 5/2000 | Seidler |
| D424,932 S | 5/2000 | Seidler |
| D429,148 S | 8/2000 | Seidler |
| 6,182,422 B1 | 2/2001 | Andersen et al. |
| 6,338,234 B1 | 1/2002 | Muise et al. |
| 6,607,696 B1 * | 8/2003 | Hamilton et al. ............. 422/37 |

FOREIGN PATENT DOCUMENTS

| WO | WO 01/79002 A1 | 10/2001 |
| WO | WO 03/022979 A1 | 3/2003 |

* cited by examiner

*Primary Examiner*—Jacob K. Ackun, Jr.

(57) ABSTRACT

Protective flexible packaging is designed to allow a consumer to determine the presence or absence of an odor in a packaged object. The object is preferably a device used for emitting a volatile active material such as a fragrance and the flexible packaging is preferably a shrink wrap material. The objects are wrapped with a shrink wrap having openings comprising no more than 10% of the total surface area of the shrink wrap film on the object. Through the use of the instant invention consumers can sense the olfactory quality of a product while the product is substantially protected during shipment, storage, and display.

14 Claims, No Drawings

SHRINK WRAP WITH SAMPLE HOLES

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

Protective wrap is utilized on a variety of products that are utilized for the dispensing or dispersal of volatile materials. These materials are packaged to protect the goods from damage, and to preserve the contents of the product. One of the problems of such packaging is the fact that the buyers of such goods can not readily determine the scent of the product they are purchasing, and thus determine whether or not the scent or scents of the product are suitable from a personal perspective One of the conventional methods of protecting dispensers utilized for the dispensing or dispersal of volatile materials is to place a continuous sheet of a shrink wrap type plastic over the product. This normally clear plastic film may or may not contain printing or other designs. For instance, in the case of a candle, the shrink wrap may be applied directly to the wax surface and may in addition advantageously hold a consumer warning label onto the product, giving both safety and use instructions. The same is true of an air freshener device such as a gel air freshener. Here the shrink wrap packaging may prevent the activation of the unit prior to purchase, or the opening or damaging of the freshener prior to purchase and/or use. The same is true of devices that are utilized for the dispersal of insecticides, sanitization chemicals, and the like.

While such wraps have been successfully used in the offering of these types of products for sale, as stated above, one of the disadvantages of the use of a shrink wrap material is the problem associated with allowing the consumer to test or smell the product through the film. While solutions to this problem have been attempted, none are believed to have offered satisfactory solutions. One method is to apply a so-called scratch and sniff label to the goods where the label contains the fragrance contained in the device. Other methods have included supplying product samples at the point of sale, or, simply providing the consumer with a sample of the goods, allowing the consumer to sample the goods being offered for sale, often times spoiling an otherwise saleable unit.

I have discovered that a modified shrink wrap film containing sample holes can be applied to fragrance emitting devices which will allow the consumers to determine their personal fragrance or active ingredient preferences while only exposing a small percentage of the device.

I have further discovered that modified shrink wrap film can be applied to devices utilized for the dispensing of volatile active materials which film will act to protect the device, and will allow consumers to sample the fragrance or odor of a given product.

Further goals and objects of this invention will be discussed later in this specification.

BRIEF SUMMARY OF THE INVENTION

This invention is directed to a device or object having disposed thereon a protective flexible plastic packaging material, said packaging material having disposed thereon one or more holes having a surface area less than 10% of the total surface area of the packaging through which a consumer can sense the presence or absence of an odor in said object without opening the packaging for such object.

This invention is also directed to a device having a protective flexible film packaging material placed thereon, wherein the device is capable of emitting one or more volatile active ingredients and each of the volatile active ingredients has an individual odor characteristic, the flexible film packaging material comprising a flexible plastic wrap having disposed therein one or more openings through which a consumer can sense the volatile active ingredient.

This invention is also directed to providing an improved method for the packaging of a volatile active ingredient emitting device with a protective flexible film packaging material, the improvement comprising wrapping the volatile active ingredient emitting device with a protective flexible film packaging material having disposed thereon one or more openings, the circumferences of such openings having no sharp edges, at locations proximate to each individual volatile active ingredient so that a consumer may smell each volatile active ingredient using his or her olfactory sense when such user's nose is placed at or near said openings. The invention allows the wrap to protect the product during shipment, storage, display and sale while allowing the consumer the benefit of sampling the fragrance before making a purchase decision.

THE INVENTION

In its broadest form, the invention is directed to a shrink wrap covering for an object, the wrap having openings which allow a consumer to sense the presence or absence of a scent or odor. This invention is directed to a flexible plastic packaging material protective covering for devices utilized for the dispensing or dispersing of a volatile active substance. The flexible plastic packaging material is preferably a shrink wrap film. This invention allow for the protective plastic wrap to be applied to a device to protect a device from inadvertent or intentional activation during shipment, storage or display, and further protects certain devices from damage which can include scratching, or other minor damage occurring during the handling of the product. While in a preferred embodiment the device is a candle, and specifically a multilayered, multifragranced candle, it is within the scope of this invention to apply the film to such items as scented candles such as those offered for sale under the Glade®, trademark by S. C. Johnson & Son, Inc.; and, gel air fresheners such as Renuzit® LongLast™ Adjustables and RoomMate® Liquid Air Fresheners (both available from the Dial Corporation), and Wizard® Crystal Air™ Air Fresheners, Wizard® Stick-Ups® Air Freshener (both available from Reckiff-Benckiser plc). As used herein the term "device" and term "object" may be used interchangeably to describe a product that is to be shrink wrapped using the instant invention. Likewise, as used herein, the terms fragrance and scent are used interchangeably. The film may be applied to the object itself in the case of, for example a pillar candle, or, may be applied to a container holding the object. The object or device may thus be a container holding a fragranced product, or it may mean the fragranced product itself.

The invention may also have use in wrapping other devices where a positive fragrance or the absence of a fragrance is important in the consumer's purchasing decision such as facial tissues, potpourri, scented cloths, and the like. As stated above, in a preferred mode of practicing the invention the film is applied to multilayered, multiscented candle products, but the invention may also find applicability in the wrapping of one layer free standing votive, pillar or jar candles, the wrap being applied to offer a degree of protection and the holes contained within the wrap offering the consumer benefit of allowing the consumer to determine his or her preference to the candle's scent. In addition, the wrap, when properly printed, can be used as the product's label.

A general overview of the shrink wrap process including methods of applying wraps, the chemical composition of wraps and the like is explained in Handbook of Package Engineering Technomic Publishing Company, Inc., Lancaster, Pa. 1998, pages 68–73. The films useful in this invention can be of any known type so long as the resultant film protects the item being wrapped, is compatible with the item being wrapped, and can be applied to the object or device within the heat parameters used to shrink the film without damaging the device or object. Films useful in this invention are those commercially available including, for example and not by way of limitation, low density polyethylene, high density polyethylene, polyethylene, polypropylene, polyesters, polystyrene, orientated polystyrene, and polyvinyl chloride. It is beyond the scope of this specification to explain or list all of the various shrinkable films that are commercially available and may be utilized in the practice of this invention. The films utilized can have a tensile strength typically ranging from about 8,000 psi (MPa) to as much as 30–40,000. The films may have an elongation percent ranging from about 40% to as much as 130–160%. The films should be strong, having a tear strength depending upon the application to which the film is to be applied, but generally ranging from as low as 3 to as high as 100 g/mil. The films employed in this invention generally have a maximum shrink of between about 40–90% and preferably from about 45 to about 80%. Additionally, the films generally have a shrink tension, as expressed in psi of between about 100 to about 2000 and preferably from about 200 to about 1500 psi. The films can be purchased in a variety of thickness ranging from <50 nm where the film is difficult but not impossible to auto machine apply to thicknesses of >70 nm where the film is thick enough to auto apply, but care must be taken in selection because of the time and temperature necessary to shrink which could be detrimental to heat sensitive articles such as candles. Lastly, the films generally have a shrink temperature ranging between about 150° to about 300° F.

Shrink wrap film is available from a variety of commercial sources. The largest commercial sources are believed to be Sleever International, Klockner, and Bonset. Shrink wrap films, and equipment used to apply the film are widely available from many commercial sources. Variables to consider in selecting a film for use in this invention are environmental (for example in selecting PVC type films), compatibility with the object being wrapped (fragrance oils in scented candles are known to attack polystyrene and therefore may add risk to long term integrity of the resultant package), shape of the object to which the film will be shrink (i.e.: the various film materials have different shrink ratio characteristics that may allow for more dramatic changes in wall surface contours). In addition to shrink films, broad film alternatives (not necessarily shrinkable) such as polyolefin, PET (poly (ethylene terpthalate), PS (poly styrene), PP (poly propylene), HDPE (high density polyethylene), and cellophane may be used.

A preferred film for use in this invention is a polyethylene terephthalate glycol available from Sleever International, Toronto, Canada designated as PET SF 060. This film is reported by the manufacturer to have a specific gravity of 1.29 g/cm$^3$, haze 5.0, heat shrinkage at 110° C. Machine Direction 6%, transverse direction 67%, elongation at break (%) machine direction >330; transverse direction 58; a thickness of 60 micrometers (um); load at break (kN): Machine Direction N/A; Transverse Direction 0.220; Tear strength (nM): Machine Direction 2150; Transverse Direction 260; Dart Impact (grams): >1450.

The films are generally mono-layered due to the different shrink characteristics of each resin present when films having different layers of different compositions are utilized. The feature unique to the wrap of this invention however is that holes or openings must be placed in the wrap so that the wrap is open to the atmosphere at certain locations, generally proximate to the portion of the wrapped product which emits a fragrance, perfume or scent, so that the consumer can smell the product using his or her olfactory senses. The film or protective wrap of this invention must accordingly be perforated so as to allow vapor from the product to escape to the consumer's nose. Because strength and integrity of the film must be maintained, generally the perforations or holes that are placed in the film must be in no greater than 10% of the surface area of the film when the film is shrunk onto the object, and preferably no greater than 5% of the surface area of the film or package area. Most preferably no more than 1% of the surface area of the film or package is perforated. In an especially preferred embodiment the film or package should have between 0.25–0.75% of the surface area of the package and/or film perforated.

The perforations in the film or package may be of almost any size or shape, provided that the perforations have no sharp corners or angles which would allow the film or package to tear at an angle's corner point(s). Preferred shapes for the perforations are accordingly those which have rounded or smooth changes in direction such as circles, ovals, or the like. A preferred perforation shape for the holes found in the film is round, and such holes can be easily placed into the film, before the film is applied to the product by stamping circle shapes out of the film in appropriate locations which will have to be determined for each application to a product. In the commercial application of this invention, depending upon the nature of the device to be wrapped as little as one hole or opening in the film per device or object to be wrapped may be required, or, in the case of a multiple scented product, multiple holes may be required. In a preferred embodiment of this invention a three layered pillar candle is wrapped with a film containing 6 holes, with the diameter of each hole being approximately 6 mm prior to the shrink process. Three holes are placed on center from the bottom cut edge of the film so as to be present at each layer of the candle. Another set of three holes is placed apart from the first set, generally approximately 180 degrees from the placement of the first set. Making the openings is accomplished by utilizing a punch having appropriately sized dies to the film. The film in this case is sleeved so that all 6 holes are punched in one operation. Sleeving the films of this invention is preferred, but not required in the practice of this invention.

The films or packaging may be utilized on a variety of products. Among the products on which this invention is believed to have the greatest applicability are gel air freshener devices, candles, candle jars containing candles, and the like. For example, one common commercially available gel air freshening device is a Renuzit® air fresheners. These "cone" shaped fresheners are packaged so that consumers can slide the air freshener out of its card board or chip board packaging, opened, smelled to sample the fragrance, closed, and reinserted into its packaging. One of the problems inherent in allowing consumers to open and close devices of this type on a store shelf however is the fact that in closing the dispenser it can be closed off center, damaging the gel with an edge of the top rigid plastic cone container impinging the gel contained in the bottom/interior of the freshener. This damage may make the product difficult to sell. The wraps of the instant invention help to prevent unauthorized opening of the unit, and thus may help to prevent damage, while allowing the consumer to use his or her olfactory sense to sample the fragrance of the air freshening device.

Another potential application, in fact the preferred embodiment of this invention is to apply the wrap/packaging to products such as multi layered candles where each layer of a candle may employ a different fragrance. Such candles are available from a variety of sources including Renuzit® Designs Pillar Candles which are available from the Dial Corporation, and Glade® 3 in 1™ Candles available from S. C. Johnson & Son, Inc. Here the packaging/film of this invention may be designed to provide perforations or openings located proximate to each layer of the candle, allowing a consumer to test or sample the individual fragrances contained in each candle section while at the same time protecting the candle from damage during handling or use. Additionally, and as stated above, the absence of fragrance or odor may be a desirable characteristic of a product. Wrapping a fragranced product with the perforated films of the invention will allow the consumer or ultimate user to determine the presence or absence of an undesirable fragrance material.

Flexible plastic wraps, bags, and shrink wraps can be utilized without departing from the spirit and scope of this invention, so long as the product being wrapped is protected by the wrap and a consumer can sample the presence or absence of a fragrance in the product.

In the practice of this invention a suitable shrink wrap film is typically selected. This film is then perforated. The film may then be sleeved to fit the product to be wrapped, or the film may be used as a wrap, generally an upper wrap and a lower wrap which layers can later be welded by heat during the shrink wrap process. The object wrapped with the wrap, is then subjected to heat, generally by placing the object on a conveyer passing through a heated tunnel for a known period of time. The heat causes the film to shrink, conforming the shape of the film to the object. Sometimes two heat treatments are utilized, one to initially form the wrap over the object, the second to remove any wrinkles from the resultant wrap and to make sure that the wrap adheres to the object. After heat treatment, the objects are cooled. In selecting films it is important that the film selected shrink at a suitable temperature at which the goods to which it is to be applied are not damaged. This is especially important for items such as candles which can be damaged by excessive heat. I have found that by carefully managing the heat applied the duration at which the heat is applied, the method can be satisfactory utilized on paraffin candles that melt at relatively low temperatures. The appropriate film to utilize, temperature to shrink the film on the object, and the temperature to which the object can be exposed can be determined by experiment knowing the properties of the particular film being utilized and the object being wrapped.

As stated above, it is often advisable to perforate the shrink wrap prior to applying the film to the object to be wrapped. Typically the holes in the film may be punched out using punches or dies to produce holes of a desired size having a rounded nature. The waste punched material may be advantageously recycled. The placement of holes in the wrap must be considered prior to application to the object being wrapped. The holes should be made in the wrap so that the holes will be at one or more locations in the wrap that after shrinking will be at locations at which sampling of the fragrance or lack of fragrance is desired. Experimentation may be required since the films are intentionally shrunk on application possibly moving the location of the hole on application.

The holes produced in the shrink wrap prior to application to the device or item to be wrapped may be of any size taking into account the surface area of the film to be punched and the guidelines above. In selecting the size of the hole it should be taken into account that the hole may shrink or expand when the wrap is shrunk onto the item being wrapped. Holes as small as a $\frac{1}{32}$ or $\frac{1}{16}$ inch diameter to as large as $\frac{1}{4}$ to $\frac{1}{2}$ inch may be used. It is important to take into account that the principal use of the wrap is to protect the item or device, and that fragrances and/or the absence of a fragrance may then be determined by the human nose at low concentrations and hence the holes applied to the wrap are generally selected to be as small as possible to afford maximum protection to the article. In selecting particular shrink wrap materials and the amount and or number of holes to apply to an item routine experimentation may be effectively utilized to optimize the protective features of the wrap when shrunk onto the item while providing suitable openings for sampling the fragrance or lack of fragrance. It is also important to note that the holes or openings may change size and or shape during the shrink process In order to illustrate the invention, the following example is presented. This example illustrates the shrink wrapping of a three layer Glade® 3 in 1™ pillar candle using Sleever International PETG film, PET SF060 described above.

Prior to shrink wrapping, the film is reverse printed with a label and wound upon a roll. After curing the roll is unwound, slit and formed into a sleeve by means of solvent seaming. Solvent seaming to form sleeves is well known. The solvent is used to bond the PETG film onto itself to form a single tube of a sleeve, which is rolled onto a reel. The flat tube sleeve reels are placed on sleeve application equipment. This equipment is designed to keep the flat tubed sleeves taught, and the sleeves pass through the sleeve applicator by way of pinch rollers and dancer bars that keep the tubing flat and taught. The flat tubed sleeve then passes through an apparatus that punches the scent holes by means of a rotary cylinder with a registered set of punches or perforators.

This process punches holes in two layers of the film encompassing the sleeve. The holes are arranged to place 6 holes, each having a diameter of 6 mm into the sleeve. Three holes are placed (on center) from the bottom cut edge respectfully at 24 mm, 56 mm and 88 mm. Vertical spacing apart from each hole is 32 mm on center. Another three holes with horizontal spacing apart from the first set of three vertically aligned holes is 101 mm on center, respectfully from the given bottom cut edge as well. The holes are placed with the understanding that they expand slightly irregularly and not scientifically measurable, upon being heated due to the force hot air blown through the holes during the shrink process making them expand. The closer the holes are to each other may cause irregular shrinking in the form of visual "wrinkles", however it is an art, not a science as to what the effects will be dependent upon the size, shape, amount of desired shrink and contour of the product to which it is shrinking onto, and experimentation is routinely required to optimize film placement, temperature, hole size, hole placement, and the like.

The punches or perforators cut out a given section of the flat tubed film, and more specifically through two layers of film, that creates the "holes(s)" registered by means of a constant repeat UV registered ink to a specific diameter and spacing as described above, resulting in an area in which the consumer can smell the fragrance contained in the object at 180° apart or opposite sides. The die punches are like the ones used in industrial paper punching apparatus and extremely sharp. The punched out pieces are vacuumed out of the cut area so as to not leave the pieces attached to the film and consistently leave an open scent hole when later applied to the candle.

Upon exiting the perforator, the sleeve is pulled over a tetrahedron (mandrel) by means of pinch rollers. The tetrahedron is used to open the flat tubed sleeve so as to expand and create a cylinder. The sleeve is then cut to a length of 115 mm. The cut, 115 mm cylindrical sleeve is indexed over the candle which is indexed below via a star wheel on a conveyor, and placed over the candle by means of a plunging apparatus which forces the sleeve to hit and stop at the base of the candle.

The sleeved candle then conveys through a heat tunnel so that the wrap can shrink around the candle. Upon first entering the heat tunnel the base of the candle and sleeve is hit by a narrow jet of hot air on two sides to cinch the bottom of the sleeve to the bottom chamfer of the candle. This cinching is done to maximize the amount of longitudinal shrinking and thus limits the rise of the sleeve when heat is applied. At the same time a downward force of hot air, with a temperature of approximately 160° C. blows open the sleeve space around the candle as the heat up the film from the inside and is then hit by the same 160° C. hot air from two sides as well. Altogether the wrap starts to shrink the film around the candle as evenly as possible.

Within the same heat tunnel the candle, now having a shrunk sleeve placed thereon is conveyed through a second heat zone having a temperature of approximately 230° C. which further shrinks the sleeve to tighten the sleeve around the candle, reducing the amount of wrinkling. The total dwell time within the heated tunnel is approximately 13.6 seconds. The heating time and temperature will be dependent upon the size of the object wrapped, the type of film selected, and the desired shrink appearance. For example, PVC films generally tend to require less heat to shrink as PVC films typically have a shrink ratio less than that of PETG.

After exiting the tunnel, the candle, now wrapped and having the openings of this invention is cooled, and packaged for shipment.

INDUSTRIAL APPLICABILITY

The invention is related to the packaging of goods for sale.

I claim:

1. A device having a protective flexible film packaging material placed thereon, wherein the device is capable of emitting a plurality of different localized volatile active ingredients at a plurality of locales, respectively, the flexible film packaging material comprising a flexible plastic wrap having an opening disposed thereon proximate each of at least two of the volatile active ingredient locales through which a consumer can sense the volatile active ingredient.

2. The device of claim 1 wherein the device is a scented candle.

3. The device of claim 2 wherein the openings in the protective flexible film comprise no more than 10 per cent of the total surface area of the protective flexible film.

4. The device of claim 2 wherein the openings in the protective flexible film comprise no more than 1 per cent of the total surface area of the protective flexible film.

5. The device of claim 1 wherein the emitting device emits an active ingredient selected from the group consisting of fragrances, sanitization agents, and deodorizing agents.

6. The device of claim 1 wherein the protective flexible film is shrink-wrap.

7. A volatile active ingredient emitting device having an odor characteristic and having a protective film packaging material placed thereon, wherein the packaging material comprises a flexible plastic wrap having disposed thereon a plurality of openings comprising no more than one per cent of the total surface area of the film through which a consumer can sense the volatile active ingredient, and wherein the device is a scented candle.

8. The volatile active ingredient emitting device of claim 7 wherein the device is a multi-layered multi-scented candle and the protective flexible film is a shrink wrap film.

9. The device of claim 6 wherein the shrink-wrap is selected from the group consisting of polyethylene terephthalate glycol, oriented polystyrene, polystyrene, low density polyethylene, high density polyethylene, polyethylene, polypropylene and poly vinyl chloride.

10. The volatile active ingredient emitting device of claim 8 wherein each layer of the candle has a different volatile actives ingredient, the volatile actives ingredients are fragrances, and wherein there is an opening in the shrink wrap film proximate to each layer of the candle.

11. The volatile active ingredient emitting device of claim 10 wherein the candle has three layers.

12. A volatile active ingredient emitting device having a protective flexible film packaging material placed thereon, the device including a volatile active ingredient having an odor characteristic, the packaging material comprising a plastic film having a total surface area and having disposed therein a plurality of openings so as to allow an end user to smell the volatile active ingredient thorough the film, wherein the openings comprise less than approximately one percent of the total surface area.

13. The volatile active ingredient emitting device of claim 12 wherein the flexible protective film is a shrink wrap and the volatile emitting device is a gel air freshener contained in a plastic container.

14. The volatile active ingredient emitting device of claim 12 wherein the emitting device is a home cleaning implement and the volatile ingredient is a fragrance.

* * * * *